(12) United States Patent
Chan et al.

(10) Patent No.: US 7,819,855 B2
(45) Date of Patent: *Oct. 26, 2010

(54) CATHETER FOR MODIFICATION OF AGENT FORMULATION

(75) Inventors: Tai Wah Chan, Palo Alto, CA (US); Tim Nelson, Los Gatos, CA (US); Jim Brown, Los Gatos, CA (US)

(73) Assignee: Durect Corporation, Cupertino, CA (US)

( * ) Notice: Subject to any disclaimer, the term of this patent is extended or adjusted under 35 U.S.C. 154(b) by 305 days.

This patent is subject to a terminal disclaimer.

(21) Appl. No.: 11/731,235

(22) Filed: Mar. 29, 2007

(65) Prior Publication Data

US 2007/0185473 A1 Aug. 9, 2007

Related U.S. Application Data

(60) Division of application No. 10/681,622, filed on Oct. 7, 2003, now Pat. No. 7,250,043, and a continuation of application No. 09/917,395, filed on Jul. 26, 2001, now Pat. No. 6,629,969.

(51) Int. Cl.
*A61M 31/00* (2006.01)
(52) U.S. Cl. ..................................... 604/508
(58) Field of Classification Search ............... 604/500, 604/502, 503, 508, 892.1, 265, 266, 264, 604/269
See application file for complete search history.

(56) References Cited

U.S. PATENT DOCUMENTS

| | | | |
|---|---|---|---|
| 5,523,092 A | 6/1996 | Hanson et al. | |
| 5,607,696 A | 3/1997 | Rivera et al. | |
| 5,609,885 A | 3/1997 | Rivera et al. | |
| 5,707,385 A | 1/1998 | Williams et al. | |
| 5,783,213 A | 7/1998 | Rivera et al. | |
| 5,868,720 A | 2/1999 | Van Antwerp et al. | |
| 5,925,552 A | 7/1999 | Keogh et al. | |
| 6,030,362 A | 2/2000 | Boussignac et al. | |
| 6,176,842 B1 | 1/2001 | Tachibana et al. | |
| 6,206,915 B1 | 3/2001 | Fagan et al. | |
| 6,348,042 B1 | 2/2002 | Warren, Jr. | |
| 6,364,856 B1 | 4/2002 | Ding et al. | |
| 6,629,969 B2 * | 10/2003 | Chan et al. | 604/508 |
| 6,738,661 B1 * | 5/2004 | Nyhart, Jr. | 604/20 |
| 2001/0041870 A1 | 11/2001 | Gillis et al. | |

OTHER PUBLICATIONS

Michaels, et al. "A Thermodynamic Method of Predicting the Transport of Steroids in Polymer Matrices," AIChE Journal (1975) 21;1073-1080.

* cited by examiner

*Primary Examiner*—Matthew F Desanto
(74) *Attorney, Agent, or Firm*—Thomas P. McCracken

(57) ABSTRACT

The present invention provides a catheter for use in delivering formulation that allows modification of the formulation prior to or concomitant with its transport or at a delivery site. The catheter comprises an elongate body, which defines an inner lumen extending between the proximal and distal ends, and a modifying element, which provides for modification of one or more components of a formulation prior to or concomitant with release at the delivery site.

18 Claims, 4 Drawing Sheets

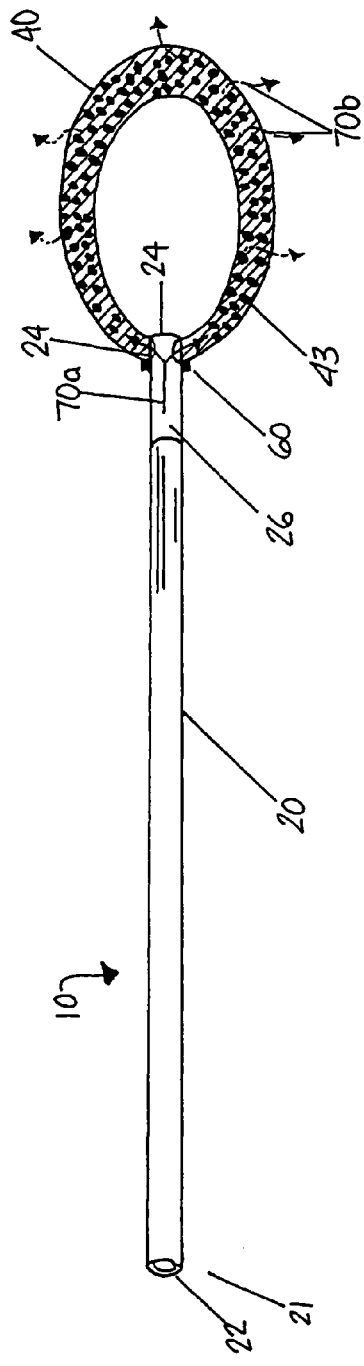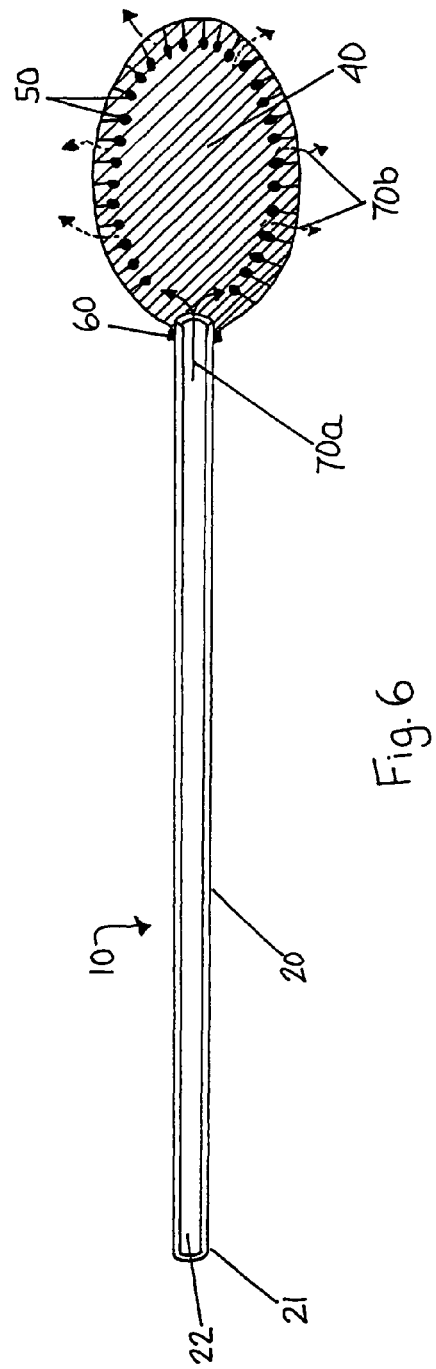

CATHETER FOR MODIFICATION OF AGENT FORMULATION

This application is a divisional application of U.S. application Ser. No. 10/681,622, which was filed on Oct. 7, 2003, now U.S. Pat. No. 7,250,043, and is a continuation of U.S. application Ser. No. 09/917,395, which was filed on Jul. 26, 2001, now U.S. Pat. No. 6,629,969 granted on Oct. 7, 2003, all of which applications and patents are hereby incorporated herein by reference.

FIELD OF THE INVENTION

This invention relates generally to drug delivery devices and methods of use relating to same, and more particularly relates to a catheter for delivery of an agent formulation requiring modification of the agent formulation prior to delivery.

BACKGROUND OF THE INVENTION

Precise and accurate delivery of drugs or therapeutic agents to a specific treatment site within a subject represents a substantial challenge in the design of drug delivery systems. Site-specific drug delivery can be particularly challenging when the drug is to be delivered to the subject long-term, e.g., over several hours to several days, weeks or months.

One approach to long-term site-specific drug delivery involves the use of implantable delivery systems, e.g., electrochemical, electromechanical, biodegradable or osmotically-driven drug delivery devices. While these implantable systems avoid the need for repeated injections often associated with long-term drug therapy administration, they have a number of limitations. First, the treatment sites which they can access are limited. In addition, sites to which drug delivery is required can be fragile, sensitive or inaccessible and thus often not amenable to insertion of an implant. The size of the delivery device can also be problematic, since the size of a reservoir large enough to contain an amount of drug sufficient to provide weeks to months of delivery can be quite large and impracticable. Smaller reservoirs can be used and the reservoir refilled with drug during the course of the treatment; however, manipulating, re-filling and/or re-positioning an implantable device can have serious consequences, e.g., increased risk of infection, patient discomfort, and increased costs.

An alternative approach is to provide formulations having high concentrations of drug, such that delivery of small amounts of formulation are sufficient to provide for a desired therapeutic effect. The total amount of formulation required for long-term therapy is thus substantially decreased, thus minimizing the size requirements for the reservoir of the device used to accomplish delivery. While this approach has met with some success, there are still serious limitations for certain therapeutics and for chronic delivery. For example, formulations with high concentrations of drug can be toxic to cells at the delivery site, or can result in irritation, inflammation, and tissue damage at the delivery site. Many drugs are insoluble or unstable at physiological pH (e.g., around pH 4-pH 8), and can only be stored long term in formulations of non-physiological pH (e.g., pH less than about pH 4, or pH greater than about pH 8). Delivery of such non-physiological pH formulations can cause adverse side effects, particularly at the delivery site. In addition, many drugs are stable as inactive prodrugs, but are relatively unstable once modified to the active species. However, providing a drug delivery device with a means for converting the prodrug to an active drug can add to the size and bulkiness of the device. Furthermore, where the delivery site is far from the drug delivery device, the stability of the active drug may be compromised during the course of its transit to the delivery site.

There is thus a need in the field for devices that allow the use of a smaller drug reservoir and highly concentrated, stable drug formulations, provide for safe delivery of same to a treatment site for long-term therapy, and provide for an efficient means for modification of the drug (e.g., from a prodrug to an active drug, modification of the formulation to a physiologically relevant pH, to an active and physiologically relevant state prior to release into a body structure, and the like).

SUMMARY OF THE INVENTION

The present invention provides a catheter for use in delivering formulation that allows modification of the formulation prior to or concomitant with its transport or at a delivery site. The catheter comprises an elongate body, which defines an inner lumen extending between the proximal and distal ends, and a modifying element, which provides for modification of one or more components of a formulation prior to or concomitant with release at the delivery site.

In one embodiment, the modifying element modifies the formulation by allowing for passage of water from the environment of use through a wall of the modifying element and into the inner lumen, thereby diluting the formulation. In a related embodiment, a modifying agent is associated with the wall of the modifying element such that influx of water through the wall displaces the modifying agent, carrying it into the inner lumen where it mixes with the formulation.

In another embodiment, the modifying element has immobilized modifying agent (e.g., immobilized on an inner wall of the modifying element) such that passage of formulation through the inner lumen results in modification of the formulation or a formulation component(s).

In one aspect, the catheter is provided in connection with a drug delivery device to comprise a drug delivery system whereby the drug delivery device and the catheter are operatively connected to provide for delivery of drug from a reservoir in the drug delivery device, through the catheter, and to the delivery site. The drug delivery device may be completely or partially implanted, or may be retained at a site external to the body with at least a portion of the catheter implanted to direct the agent to the desired delivery site within the body. An exemplary drug delivery device for use in the system is configured to have at least one compartment for storing the formulation, e.g., a reservoir.

In another aspect, the present invention provides a method for delivery of a drug or therapeutic agent to a treatment site in a subject by implanting at least the distal end of a catheter of the invention at a desired delivery site and introducing a drug or agent to the delivery site through the catheter. The catheter can be used to dilute an agent in the formulation and/or increase the surface area of release prior to delivery to a delivery site, thus reducing side effects that may be caused from the delivery of a concentrated drug to a site.

In another aspect, the invention features a method for modifying an agent formulation prior to delivery to a subject by implanting at least a distal portion of a catheter according to the invention at a delivery site in a subject, and introducing a formulation comprising an agent into the inlet of the elongate body. The introduced formulation flows through the elongate body passageway and past an inner wall of the modifying element so as to effect modification of the formulation or the agent (or other component) in the formulation is modified prior to release at the delivery site in the subject. The formulation or formulation component can be modified by, for example, dilution during transit through the catheter, increasing or decreasing pH prior to exit at the delivery site, or, where the agent is a prodrug, the prodrug is converted to an active drug prior to exit at the delivery site.

A primary objective of the invention is to provide a catheter that can facilitate delivery of formulations comprising high concentrations of a drug or other agent with minimal detriment to the surrounding tissue.

It is another object of the invention to provide for modification of a formulation component prior to delivery to a delivery site, e.g., conversion of a prodrug to an active drug, adjustment of pH, or for dilution of a formulation immediately prior to delivery to the delivery area.

Another object of the invention is to provide a drug delivery system that can be readily handled, implanted and adapted for use in accurate, consistent and reliable delivery of drug at a particularly low volume rate, e.g., microliter or submicroliter quantities of a formulation per day.

It is yet another object of the invention to provide a drug delivery system compatible for use with a highly concentrated drug formulation so that a smaller drug reservoir volume of the drug delivery device is required, thereby reducing the volume of formulation and the size of the drug reservoir that must be in the drug delivery device, while allowing dilute or physiologically active and non-toxic drug formulation to be delivered at the site of desired action. This permits reduction in size of the entire drug delivery device, thus increasing comfort and mobility for the patient.

It is another object of the invention to provide a catheter that is suitable for delivery of drug to a distal delivery site within a subject, particularly sites that are highly sensitive or fragile, e.g., the spinal cord. It is yet another object of the invention to provide a mechanism by which inactive drug can be stored in a drug reservoir and converted to an active state prior to delivery to the delivery area.

Another object of the invention is to provide a catheter that can be used with a variety of drug delivery devices.

An advantage of the invention is that the catheter can facilitate delivery of extremely small volumes of drug, e.g., submicroliter volumes, and at low volume delivery rates, yet is easily handled, e.g. by a clinician during implantation.

Another advantage of the invention is that an inactive form of a drug can be stored in a drug reservoir and converted to an active state prior to delivery. This advantage allows stable, inactive formulations to be stored and converted to less stable, active states just prior to delivery.

These and other objects, advantages and features of the present invention will become apparent to those skilled in the art upon reading this disclosure in combination with the drawings, where like numerals refer to like components throughout.

BRIEF DESCRIPTION OF THE DRAWINGS

FIG. 5 is a partial cut-away view of a catheter of the invention comprising an elongate body comprising and operatively attached to a ring-like modifying element.

FIG. 6 is a cut-away view of a catheter of the invention comprising an elongate body comprising and operatively attached to a bulb-like modifying element.

DETAILED DESCRIPTION OF THE INVENTION

Figure 1:
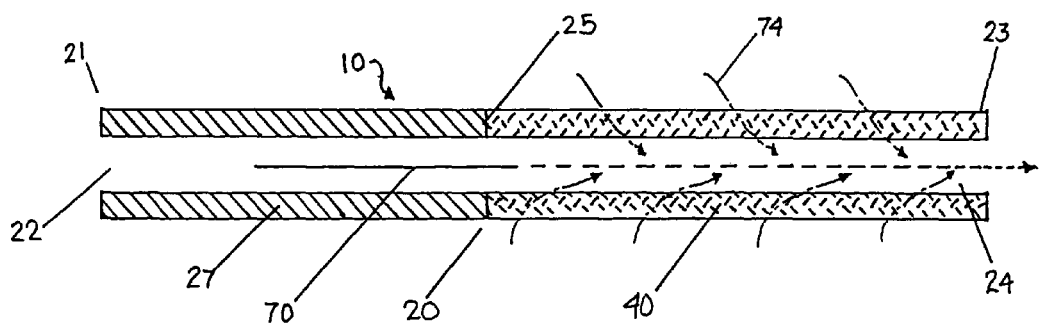
FIG. 1 is a cut-away view of a catheter of the invention comprising an elongate body comprising a selectively water permeable modifying element to effect dilution of formulation during its transit through the flow pathway.

Before the present invention is described, it is to be understood that this invention is not limited to the particular embodiments described, as such may, of course, vary. It is also to be understood that the terminology used herein is for the purpose of describing particular embodiments only, and is not intended to limit the scope of the present invention, which will be limited only to the appended claims.

It must be noted that as used herein and in the appended claims, the singular forms "a", "an," and "the" include plural referents unless the context clearly dictates otherwise. Thus, for example, reference to "a catheter" includes one or more catheters within an assembly, reference to "a formulation" includes mixtures of different formulations, and reference to "the method of delivery" includes reference to equivalent steps and methods known to those skilled in the art, and so forth.

Unless defined otherwise, all technical and scientific terms used herein have the same meaning as commonly understood by one of ordinary skill in the art to which the invention belongs. Although any methods and materials similar or equivalent to those described herein can be used in the practice or testing of the present invention, the preferred methods and materials are now described. All publications mentioned herein are incorporated by reference to disclose and describe the specific methods and/or materials in connection with which the publications are cited.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Definitions

The term "delivery site" is generally meant to refer to the specific area of the body to which the drug, drug formulation, or other agent is introduced, i.e. through a device of the present invention. The delivery site may be a discrete area (e.g., an area at the distal tip of the catheter) or a somewhat larger area surrounding the device (e.g., the device provides for delivery along either a portion of or its entire length).

The terms "treatment site" or "target site" as used herein interchangeably to mean the desired site of action of the substance to be delivered. The treatment site may be the substantially the same as the delivery site, or may be some distance from it (e.g., adjacent to the delivery site, or within a distance from the delivery site that can be reached by diffusion or other transport of drug from the delivery site).

The terms "access site" or "implantation site" as used herein are generally meant to refer to a site on or in a subject at which a drug delivery system of the invention is introduced for implantation and positioning within the subject's body, e.g., for delivery of drug to a desired delivery site. For example, where a device is for delivery of drug to the spinal cord, the access site or implantation site can be a subcutaneous site at which a proximal end of the device is substantially retained (i.e., with the drug delivery device), and the delivery site is in a position within or adjacent the spinal cord at which a distal end of the device is positioned for delivery of drug.

The term "drug delivery device" as used herein is generally meant to encompass any device that comprises a drug reservoir and that facilitates movement of drug from the drug reservoir to a site external to the drug delivery device. "Drug delivery device" thus encompasses controlled drug delivery devices, as well as devices that release drug in an unpatterned, e.g., substantially unregulated, manner. Controlled drug release devices are particularly preferred for use with the catheter of the present invention.

The term "delivery system" as used herein is generally meant to refer to a combination of a catheter of the invention and a drug delivery device suitable for use in the delivery of drug to a delivery site, preferably a controlled release device.

The term "impermeable" as used herein is generally meant to refer to material that is sufficiently impermeable to environmental fluids as well as ingredients contained within the dispensing device such that the migration of such materials into or out of the device through the impermeable portion of the device is so low as to have substantially no effect on the concentration, activity or function of the drug retained within the device during the delivery period.

The term "selectively permeable" as used herein is meant to refer to material that is substantially impermeable to one or more compounds, but substantially permeable to a different compound(s). For example, a material is selectively permeable for a drug when the materials allows for passage of the drug, but does not allow substantial or detectable passage of environmental fluids or agents in the fluid. In another example, a material is selectively permeable to water when the material allows passage of water, but does not allow substantial or detectable passage of other compounds (e.g., drug).

The terms "modification" or "physical or chemical modification" as used herein generally means any physical or chemical change to a formulation and/or a component(s) of a formulation, including a physical or chemical change to an agent or drug in the formulation. Examples of "modifications" include, but are not necessarily limited to dilution or solubilization of a formulation component(s) (e.g., agent); increase or decrease in formulation pH; and production of an active species of an agent from an inactive species provided in the formulation (e.g., conversion of a prodrug to an active drug).

The term "controlled release" as used herein (e.g., in the context of "controlled drug release") is generally meant to encompass release of substance (e.g., a drug) at a selected site or otherwise controllable in rate, interval, and/or amount. Controlled release encompasses, but is not necessarily limited to, substantially continuous delivery, patterned delivery (e.g., intermittent delivery over a period of time that is interrupted by regular or irregular time intervals), and delivery of a bolus of a selected substance (e.g., as a predetermined, discrete amount if a substance over a relatively short period of time (e.g., a few seconds or minutes)).

The term "controlled release device" as used herein is generally meant to encompass any device that provides for release of a drug or other desired substance in a manner that is at least substantially independent of its environment of use, and that can be adapted for use with a device of the invention.

The term "low volume rate delivery" as used herein is generally meant to refer to delivery of a liquid or semisolid drug at a volume rate of from about 0.01 µl per day to about 200 µl per day, usually about 0.04 µl per day to about 20 µl per day, more usually about 0.1 µl per day or about 8.0 µl per day.

The terms "distal" or "distal end" as used herein is generally meant to refer to components and/or structures which are closer to the delivery site, treatment site or sampling site within the body of the subject being treated.

The term "proximal" or "proximal end" as used herein is generally meant to refer to components and/or structures which are closer to a clinician or individual who is using the catheter and/or devices of the invention in a medical treatment setting.

The term "drug formulation", "agent formulation," or "formulation" as used interchangeably herein are generally meant to encompass any substance suitable for delivery to a treatment site of a subject, which substances can include pharmaceutically active drugs, as well as biocompatible substances that do not exhibit a pharmacological activity in and of themselves, but that provide for a desired effect at a treatment site, e.g., to flush or irrigate a treatment site, e.g., saline. Such drugs and/or biocompatible substances may be in an active or inactive state.

The terms "drug" or "agent" as used interchangeably herein are generally meant to refer to any drug that is conventionally administered by parenteral injection (e.g., intravenously, intramuscularly, subcutaneously, intrathecally, etc.). Drugs compatible for delivery using the devices and methods of the invention are readily apparent to the ordinarily skilled artisan upon reading the disclosure provided herein.

The term "drug delivery" as used herein is generally meant to refer to a process by which drugs or other therapeutic agents are released from devices of the invention. "Drug delivery" is thus meant to include, applying agents to areas including, although is not necessarily limited to, a subcutaneous, percutaneous, intravenous, intrathecal, intramuscular, intra-arterial, intravascular, intraperitoneal, intraspinal, epidural, intracranial, peritumoral, or intratumoral (e.g., within a cancerous growth) tissues within a subject, as well as to areas within or near a selected organ or tissue (e.g., central nervous system (e.g., spinal fluid, brain, etc.), peripheral nervous system, kidney, liver, pancreas, heart (e.g., intrapericardial), lung, eye, ear (e.g., inner ear), lymph nodes, breast, prostate, ovaries, testicles, thyroid, spleen, etc.), digestive system (e.g., stomach, gastrointestinal tract, etc.), skeletal muscle, bone, urinary bladder, gall bladder, adrenal gland, adipose tissue, parathyroid gland, uterus, fallopian tube, skin, into a vessel associated with the circulatory system (e.g., artery, arteriole, blood vessel, vein, capillary bed, lymph vessel, particularly arteries that feed a selected organ or tissue)), a tumorous growth (e.g., cancerous tumor (e.g., solid tumor), cyst, etc.), or at an area associated with a microbial infection (e.g., bacterial, viral, parasitic or fungal infection), or to an autologous or synthetic graft (e.g., a vascular graft).

The term "site-specific drug delivery" as used herein is generally meant to refer to any process by which drugs or other therapeutic agents are released from catheter assemblies and/or drug delivery devices of the invention to a target area in need of medication. Site-specific drug delivery is this meant to include, but is not necessarily limited to, therapeutically applying agents to areas comprising subcutaneous, percutaneous, intravenous, intrathecal, intramuscular, intra-arterial, intravascular, intraperitoneal, intraspinal, epidural, intracranial, peritumoral, or intratumoral (i.e., within a cancerous growth) tissues within a subject, as well as areas within or near a selected organ (e.g., central nervous system (e.g., spinal fluid, brain, etc.), peripheral nervous system, kidney, liver, pancreas, heart (e.g., intrapericardial), lung, eye, ear (e.g., inner ear), lymph nodes, breast, prostate, ovaries, testicles, thyroid, spleen, etc.), digestive system (e.g., stomach, gastrointestinal tract, etc.), skeletal muscle, bone, urinary bladder, gall bladder, adrenal gland, adipose tissue, parathyroid gland, uterus, fallopian tube, skin, into a vessel associated with the circulatory system (e.g., artery, arteriole, blood vessel, vein, capillary bed, lymph vessel, particularly arteries that feed a selected organ or tissue)), a tumorous growth (e.g., cancerous tumor (e.g., solid tumor), cyst, etc.), or at a site associated with a microbial infection (e.g., bacterial, viral, parasitic or fungal infection), or to an autologous or synthetic graft (e.g., a vascular graft).

The term "subject" as used herein is generally meant to refer to any animal to which a drug, drug formulation or an agent can be delivered, including but not necessarily limited to, a mammal (e.g., human, dog, cat, cow, etc). In one embodiment of interest, the subject is human.

The term "unintended result" as used herein is generally meant to refer to any undesirable or unanticipated reaction that would have an adverse impact on the activity or function of the drug to be delivered.

Overview of the Invention

The present invention provides a catheter useful in the administration of a formulation that requires modification prior to its transport to a delivery site (e.g., due to, for example, the non-physiologically-compatible pH of the formulation, the toxic nature of highly concentrated agent or other component in the formulation, and/or the presence of an inactive species that requires modification to an active species to provide a therapeutic effect).

In general, the catheter comprises an elongate body and a modifying element operatively associated with the elongate body. The modifying element provides for modification of formulation passed through the catheter, either through a characteristic(s) of the modifying element structure (e.g., selective water permeability of the modifying element wall) or by incorporation of a modifying agent with the modifying element. The modifying element may be associated with the elongate body of the catheter in a variety of ways and may be provided in a variety of configurations. By "associated" is generally meant a structural relationship between the elongate body and the modifying element such that they form an operative unit. For example, the modifying element may be fixedly (e.g., permanently) attached or removably attached, connected, or the like, to the elongate body. Such fixed or removable attachment or connection may be accomplished by means of adhesion, pressure, molding, snap fit, male-female connection, threading, bonding, chemical, mechanical, or other such means. In all embodiments, the elongate body and modifying element are associated so that formulation passes through the elongate body and the modifying element before it is released through the catheter outlet at the distal end.

In one embodiment, the modifying element is selectively permeable to water and substantially impermeable to ionic species such as ionized agent molecules, such that the agent formulation is diluted during its transit through the catheter. As formulation moves through the catheter of this embodiment, the formulation is diluted by water passing through the modifying element. The formulation delivered from the catheter is thus diluted, e.g., to a physiologically neutral pH formulation, prior to its exit at the delivery site.

In another embodiment, the modifying element comprises a modifying agent associated with the modifying element. The modifying agent facilitates modification of a physical or chemical characteristic of the agent to be delivered, e.g., by converting the drug from a pharmaceutically inactive to a pharmaceutically active state (e.g., conversion of a prodrug to a drug).

The catheter may be associated with a drug delivery device, to provide a drug delivery system. In this embodiment, the catheter is adapted to facilitate the delivery of drug(s) or drug formulations from a reservoir of the drug delivery device to one or more sites distal to the drug source. For example, the catheter may be introduced into a subject by navigation through a biologically defined lumen of the subject, e.g., the vasculature or the like, and the distal end positioned at a desired delivery site within the vascular system. A drug delivery device compatible with the catheter is connected so as to be in fluid communication with the catheter is positioned either internal or external to the subject, often times implanted within the subject, and the formulation is delivered via a pathway through which drug may flow from the drug reservoir of the drug delivery device, through the catheter, and to the delivery site in the subject. In embodiments of particular interest, the formulation is delivered at a low volume rate.

Each element of the catheter will now be described in more detail.

Elongate Body

The elongate body generally comprises a proximal end defining an inlet, a distal end defining an outlet, and a body defining an inner lumen between the proximal and distal ends, which inner lumen provides at least a portion of the flow pathway of the catheter. The elongate body proximal end generally also defines the catheter proximal end and catheter inlet, while the elongate body distal end generally defines the catheter distal end and catheter outlet, although variations of such are encompassed by the invention. Generally, the shape of the elongate body is substantially tubular, although the shape may vary depending on a variety of factors such as patient anatomy, delivery site, delivered drug, and the like. Shapes that may find use in the present invention include, but are not limited to, elliptical, cylindrical, or the like.

The elongate body is preferably made of a highly compliant material. Where a portion of the elongate body is exposed to tissue upon implantation, the elongate body material comprises a biocompatible material for at least that portion which is implanted. The compliant characteristic of the elongate body enables safe navigation and implantation at a delivery site, e.g., through tortuous biologically defined lumens or preformed conduits and the like, and to minimize damage to surrounding tissue or structures. As such, the elongate body can be of substantially the same degree of flexibility or stiffness throughout its length, or may vary in flexibility or stiffness over its length. The desired flexibility or stiffness of the elongate body can be varied with the particular delivery site and/or drug delivery pathway with which it is to be used.

The elongate body can comprise one or more than one piece, component, material or layer. For example, the elongate body can be provided in the catheter as a continuous element, or may be separated by a modifying element positioned between the proximal and distal ends of the elongate body. Such multiple pieces, components, materials or layers may be contiguous, partially overlapping, discretely layered, extruded, or the like and may be subsequently attached using any suitable means. In certain embodiments, the elongate body is comprised of discrete sections of differing materials and/or layers to impart various desirable characteristics, e.g., such as relative stiffness.

In general, the material from which the elongate body is made is substantially impermeable and/or completely impermeable to formulation and formulation components (e.g., agent) to be delivered through the elongate body passageway. The elongate body materials are generally selected so that they do not unintentionally react with the drug or agent to be delivered. Exemplary materials include, but are not necessarily limited to: biocompatible polymers, elastomers, metals, metal alloys, glasses, laminates of hydrophilic polymers and hydrophobic polymers, multilaminates or polymers, metal, and/or glasses, and the like. Exemplary biocompatible polymeric materials include, but are not necessarily limited to, homopolymers and copolymers of vinyl acetate (e.g., ethylene vinyl acetate copolymer); homopolymers and copolymers of acrylates (e.g., poly(methyl) methacrylate (PMMA), polyethylmethacrylate, ethylene glycol dimethacrylate, ethylene dimethacrylate and hydroxymethyl methacrylate); polyurethanes; polyethylenes; polyvinylchlorides; polycarbonates; polyamides; polysulfones; polyesters; polyimides; halogenated polymers (e.g., polytetrafluoroethylene (PTFE), polyvinyl fluoride, polychlorotrifluoroethylene, copolymers tetrafluoroethylene and hexafluoropropylene; PFA, and the like); polyolefins (e.g., high density polyethylene (HDPE), low density polyethylene (LDPE), linear low density polyethylene (LLDPE), polypropylenes, and the like); polystyrenes; nylons; homopolymers and copolymers of acrylonitrile (e.g., acrylonitrile-butadiene-styrene polymer, styrene acrylonitrile, polycarbonate-acrylonitrile-butadiene-styrene; and the like); polyvinylpyrrolidone; polyacrylonitrile butadiene; polyethylene terephtholate; polymethylpentene; polyisobutylene; polymethylstyrene; polyvinylidine chloride and homopolymers and copolymers of polyvinylidine chloride (e.g., polyvinylchloride-acrylic copolymers); PEBAXJ; HYTRELJ; and other similar compounds known to those skilled in the art. Further exemplary polymers are described in Plastics Materials 6th ed., May 1995, J. A. Brydson, Butterworth-Heinemann, publishers.

Suitable, biocompatible elastomers include, but are not necessarily limited to, biocompatible elastomers such as medical grade synthetic (e.g., silicone) rubbers; polyvinyl chloride elastomers; polyolefins; homopolymeric and copolymeric elastomers; natural rubbers; and fluorinated polymers (e.g., PTFE), and the like.

Metallic materials suitable for the elongate body comprise stainless steel, titanium, platinum, tantalum, gold and their alloys; gold-plated ferrous alloys; platinum-plated titanium, stainless steel, tantalum, gold and their alloys as well as other ferrous alloys; cobalt-chromium alloys; titanium nitride-coated stainless steel, titanium, platinum, tantalum, gold, and their alloys; TEFLON™; nickel titanium; and superelastic nickel titanium.

In one particular embodiment, the elongate body comprises nickel titanium materials, particularly superelastic nickel titanium (NITINOL™).

The elongate body may comprise additional materials, components additives or agents as well. For example, the inner lumen wall may comprise a coating to facilitate transport of drug through the lumen, or to impart other desirable characteristics, such as drug compatibility, minimizing drug adsorption to the biocompatible polymer material, and the like. The lumen can also comprise coatings that reduce the risk of infection, e.g., a silver coating, an antimicrobial agent(s), or the like. Similarly, the outer wall of the elongate body can comprise a coating or be treated to facilitate lubriciousness, reduce the risk of infection and/or to impart other desirable characteristics to the catheter. Markers or other such material may also be added to facilitate radiographic visualization of the elongate body. For example, materials such as platinum, palladium, gold or radiopaque filler materials such as barium sulfate, bismuth trioxide, bismuth carbonate, powdered tantalum, or the like may be incorporated. Similarly, the elongate body may comprise a reinforcement element(s) to provide for enhanced stiffness, to avoid kinking of the elongate body, etc. Such reinforcement element(s) can be, for example, a coil or braid that is on the outer surface of the elongate body, within a wall of the elongate body, or positioned on the inner wall of the elongate body.

As noted above, the elongate body defines an inner lumen or passageway, through which an agent is delivered. Such lumen generally lies between the proximal and distal ends and of the elongate body. In certain embodiments, the elongate body defines a single lumen; however, the elongate body may also define multiple lumen, which may vary in length and/or diameter. Where more than one lumen is present, the lumens may be contiguous, adjacent, or branching. The lumen(s) transports drug to an aperture of the elongate body for expulsion out of the elongate body.

Similarly, the elongate body can define a single delivery outlet or aperture, or two or more such outlets or apertures. Where the elongate body defines a plurality of apertures, the apertures can be situated on various sites on the elongate body, and can vary in size. In one embodiment, the elongate body has a distal aperture and a plurality of side-apertures defined by the elongate body wall. Apertures may be complete, unobstructed holes, or may be partial holes. The elongate body distal end can comprise any of a variety of shapes, and may comprise a valve, e.g., a duck bill valve, or other element to further facilitate regulation of delivery of formulation through the elongate body outlet and to inhibit back-flow into the elongate body lumen. For example, a rate-limiting membrane or valve-structure can be positioned within an outlet to prevent back-flow and/or to facilitate a regulation of formulation flow out the outlet.

The dimensions of the elongate body, e.g., length, inner diameter, outer diameter, may vary and are generally selected as a function of various factors, e.g., the delivery site, the formulation to be delivered, and the like. The outer diameter may be substantially the same throughout the entire length or may vary, e.g., taper, step, or the like. The elongate body inner diameter may vary depending on a variety of factors, one such factor being drug compatibility, e.g., molecular weight, viscosity, and other factors such as drug delivery rates, and the like. For example, in certain embodiments, the inner diameter is compatible for drug delivery at relatively low volume rates, e.g., as low as about 0.01 µl per day. Conversely, the inner diameter may be compatible for relatively higher volume rates. In certain embodiments, the rate of drug delivery ranges from about 0.01 µl per day to 300 µl per day, usually between about 0.02 µl per day to 250 µl per day. The inner diameter of the elongate body can be substantially the same throughout the entire length, or it may vary, e.g., it may be tapered, stepped or narrowed at any point along the length. For example, the inner diameter may be tapered at the distal end or widened at any point along the length, e.g., widened over a distal portion. In an exemplary, non-limiting embodiment, the length of elongate body ranges from about 0.1 inches to 80.0 inches, usually from about 2.0 inches to 60.0 inches and more usually from about 6.0 inches to 24-30 inches. In certain embodiments, the elongate body inner diameter ranges from about 0.0002 inches to 0.02 inches, e.g., from about 0.0005 inches to 0.015 inches, usually from about 0.001 inches to 0.0125 inches and more usually from about 0.002 inches to 0.010 inches. Where the elongate body is provided as an exit orifice of a drug delivery device, the length of the elongate body is measured starting from the proximal end of the elongate body which is in fluid communication with the reservoir of the drug delivery device.

The elongate body outer diameter and consequentially the circumference of the elongate body, may vary as well. In certain embodiments, the elongate body outer diameter ranges from about 0.080 inches to about 0.020 inches, usually from about 0.020 inches to about 0.070 inches and more usually from about 0.01 inches to 0.100 inches, e.g., from about 0.015 inches to about 0.030 inches to 0.060 inches. In many embodiments, the outer diameter varies from the proximal end to the distal end, e.g., tapers in diameter or decreases or increases in a step-wise fashion. In particular embodiments, the inner diameter ranges from about 0.003 inches to 0.006 inches and the outer diameter ranges from about 0.005 inches to 0.012 inches.

Modifying Element

The modifying element facilitates modification of one or more physical or chemical properties of a formulation or component thereof (e.g., a drug or agent). The physical or chemical modification facilitated by the modifying agent can be, for example, dilution or solubilization of the agent to be delivered; alteration in pH of the formulation; a change in the physical conformation of the agent being delivered; a chemical reaction that provides for conversion of an agent from a pharmaceutically inactive state to a pharmaceutically active state; and the like. The modifying agent can thus be a solvent (e.g., water or other fluid present in the environment surrounding the catheter (e.g., at the implantation site)); an enzyme; a buffer or other agent that adjusts pH; or a catalyst or other agent that can effect a desired physical or chemical modification. In one embodiment, the modifying agent activates a previously inactive drug or therapeutic agent.

By "activate" is generally meant an increase the biological activity, by, for example, altering the physical structure or conformation (e.g., to convert a prodrug to a drug), pH, etc., of the agent. For example, a drug that is unstable at or near neutral pH can be stably stored in the drug reservoir at a high or low pH and readjusted to neutrality during transit through the catheter. Similarly, an inactive protein may be stored in a stable state/conformation and then converted (e.g., cleaved, ionized, enzymatically converted, hydrolyzed, mixed with another species (i.e., agent drug), etc.), to an active state prior to delivery. Examples of modifying agents include, but are not necessarily limited to endogenous or non-endogenous enzymes (e.g., site-specific proteases, phosphatases, peptidases (e.g., carboxypeptidases) and the like). Exemplary prodrugs include but are not necessarily limited to, those described in U.S. Pat. No. 6,030,997 (describing exemplary prodrugs which are conjugates of a pharmacologically active compound and at least one blocking group, characterized by the presence of a covalent bond which is labile in the presence of an elevated concentration of hydrogen ions). The invention also contemplates delivery of pro-prodrugs (see, e.g., U.S. Pat. No. 5,877,158), which can be converted to a prodrug during transit through the device of the invention and subsequently converted to the active drug following release at the delivery site, or can be converted from prodrug and to drug during transit through the device. Additional prodrugs, as well as methods and compositions for converting prodrugs to active drug entities and methods of identifying such prodrugs, are well known in the art (see, e.g., U.S. Pat. No. 6,245,750).

The modifying element is operatively associated with the elongate body of the catheter such that introduction of a flowable formulation into the catheter inlet (e.g., elongate body inlet) results in movement through the inner lumen defined by the elongate body, bringing the formulation into contact with the modifying element at some point within the catheter flow pathway and facilitating modification of the formulation and/or of a formulation component(s).

The modifying element can be positioned at varying points within the elongate body, e.g., at or near the distal end, at or near a midpoint between the elongate body proximal and distal ends, etc. The modifying element can be positioned within or along all or a portion of the elongate body, e.g., the distal end. For example, the modifying element can define a conduit operatively associated with the elongate body, e.g., the modifying element can be a substantially tubular element that, in combination with the elongate body, defines a formulation flow pathway of the catheter. Alternatively, the modifying element can be provided as a patch-like element positioned on a portion of the elongate body wall, where the patch comprises an inner wall which is in fluid communication with the catheter flow pathway.

In another embodiment, the modifying element is provided as an extension of the distal end of the elongate body, e.g., as one or more bulb-like structures or a ring-like structures at the elongate body distal end. The modifying element can be provided in any one or combination of the aforementioned configurations. In this embodiment, the modifying element can be provided as a separable component from the remainder of the catheter. The modifying element can be operatively associated with the elongate body of the catheter by an attachment element, which can provide for fixed or removable association with the elongate body. Fixed or removable attachment or connection may be accomplished by means of adhesion, pressure, molding, snap fit, male-female connection, threading, bonding, chemical, mechanical, or other such means.

In one embodiment, the body of the modifying element defines a lumen, the body comprising a material that is permeable to formulation but substantially impermeable to modifying agent. In this embodiment, formulation flows through a flow pathway defined by the elongate body, out an elongate body outlet, and into the lumen defined by the modifying element body. The formulation contacts a modifying agent positioned within the modifying element lumen, which modifying agent may be coated or immobilized on an inner wall of the modifying element. Where the modifying element body comprises a material substantially impermeable to the modifying agent, the modifying agent can be provided as a gel or solution within the modifying element lumen so that flow of formulation into the modifying element lumen results in contact of the modifying agent with the formulation and modification of the formulation or a component(s) thereof. The modifying agent wall may optionally be substantially impermeable to unmodified formulation or formulation component, but permeable to modified formulation or modified formulation component, so that the modifying element allows for exit of substantially only modified formulation or modified formulation component (e.g., activated drug modified from a prodrug).

The modifying element can be fixed or removably attached, connected, or the like to the elongate body. Such fixed or removable attachment or connection may be accomplished by means of extrusion, adhesion, pressure, molding, snap fit, male-female connection, threading, bonding, chemical, mechanical, or other such means.

As noted above, the modifying element is generally adapted to modify a formulation or component(s) therein (e.g., drug) just prior to or concomitant with delivery to the delivery site. The modifying element can accomplish this in various ways. For example, the modifying element can comprise a selectively water permeable membrane, which membrane provides for inflow of water from the environment of use into the formulation in the flow pathway of the catheter inner lumen, resulting in dilution of the agent.

Modifying element body materials can vary according to a variety of factors such as the desired permeability (e.g., water permeability), stiffness, and the like. For example, in one embodiment, the modifying element modifies by the formulation by dilution. In this embodiment, the material of the modifying element is selected so as to be selectively permeable to water but impermeable to components of body fluids such as enzymes, peptides, proteins, etc. The ingress of water through the modifying element and into, for example, the lumen of the catheter can be utilized beneficially to dilute the effective drug concentration.

Methods for selection or adaptation of a material to provide for a desired permeability or selective permeability are well known in the art. In general, a polymer is substantially impermeable to water when the water sorption of the polymer is less than 10%. Alternatively, it is desired that the material be permeable to water but impermeable to formulation, the same polymer can be chosen of such grade that the water sorption is between 20% to 80%, making the polymer permeable to water but still impermeable to formulation or its components, e.g., enzymes or proteins.

The permeability of a formulation component (e.g., drug) through polymeric walls or membranes can be estimated from the relationship $DC_s$ and MP, where D is the diffusivity of an agent in the polymer and $C_s$ is the solubility in the polymer of the substance or agent in the formulation to be delivered, and MP is the melting point of the polymer. For a detailed discussion of this relationship and guidance as to the prediction of the transport of a substance through a polymeric material, see, e.g., Michaels et al. "A Thermodynamic Method of Predicting the Transport of Steroids in Polymer Matrices," AIChE Journal (1975) 21:1073-1080.

Generally, the materials must be compliant and biocompatible. Exemplary materials include: polyether polyurethanes, plasticized cellulose acetates, silicone rubber, silicone elastomers, ethylene vinyl acetate copolymers, polyester elastomers (Hytrel®, Dupont), PEBAX®, cellulose esters (acetate, butyrate, styrene-butadiene block copolymer (Krator® Multibase, Inc.) and typically polymers with water sorption in the range of 10% to 80% such as hydrogel materials such as HERA. Variations on these materials, or additional materials compatible with the present invention, will be readily apparent to the ordinarily skilled artisan upon reading the present specification.

The modifying element may comprise additional materials, components additives or agents as well. For example, the inner or outer walls, i.e., the inner and outer walls of the modifying element may comprise a coating to impart desirable characteristics e.g., coatings that reduce the risk of infection, e.g., a silver coating, an antimicrobial agent(s), or the like, or a coating to facilitate lubriciousness. Markers or other such material may also be added to facilitate radiographic visualization of the modifying element. For example, materials such as platinum, palladium, gold or radiopaque filler materials such as barium sulfate, bismuth trioxide, bismuth carbonate, powdered tantalum, or the like may be incorporated. Similarly, the modifying element may comprise a reinforcement element(s) to provide for enhanced stiffness, to avoid kinking, etc. Such reinforcement element(s) can be, for example, a coil or braid that is on the outer surface of the modifying element, within a wall of the modifying element, or positioned on the inner wall of the modifying element.

The dimensions of the modifying element may vary according to many factors such as dimensions of the elongate body, desired diffusion rates (e.g., rate of diffusion of water into the catheter inner lumen), malady, subject's anatomy, and the like. Where the modifying element defines a lumen, the inner diameter of the modifying element may be substantially the same throughout the entire length, or it may vary, e.g., it may be tapered, stepped or narrowed at any point along the length. For example the inner diameter may be tapered at the distal end or widened at any point along the length, e.g., widened over a distal portion or the inner diameter may be expanded to decrease drug concentration before delivery. For example, the inner diameter may contain a fluid, e.g., biological fluid from the external environment that dilutes the drug or agent.

Selectively Water Permeable Modifying Element

In one embodiment, the modifying element facilitates modification of the formulation by facilitating dilution of the formulation during its transit through the catheter. In this embodiment, the modifying element is selectively water permeable, but substantially impermeable to formulation components, particularly to agent in the formulation, more particularly to ionized drug molecules or protons. In use, water from the environment in which the catheter body is implanted passes through the selectively water permeable modifying element, resulting in dilution of the formulation components during transit of the formulation through the catheter. At the same time, the volume of diluted formulation increases in proportion to the osmotic water influx and length of the selectively water permeable portion of the modifying element wall.

The dilution ratios and pumping rate at the exit at the catheter distal end is calculated as a function of selected catheter dimensions. In general, the dilution ratio of any chemical species at an undesirably high concentration (Co) in a formulation to a more desirable concentration Cι, can be expressed as:

$$C\iota/Co = 1/(1+2\Phi o/Fo)^{1/2} \qquad (1)$$

where $\Phi o$ is the water permeation rate through the selectively water permeable portion of the modifying element wall when filled with formulation (e.g., formulation having an agent at the same concentration as in the reservoir of a drug delivery device operably attached to the catheter), and Fo is the rate of flow from the drug delivery device at the point of the catheter inlet.

For a cylindrical catheter (i.e., the elongate body and modifying element define cylindrical catheter body), $\Phi o$ is defined as $$\Phi o = (6.28 r/h)(K\Pi o)L \qquad (2)$$

where r is a mean radius of the catheter, h is the thickness of the catheter wall, K is water permeability, Πo is the osmotic pressure of the concentrated formulation in the drug delivery device, and L is the length of the selectively water permeable portion of the catheter (i.e., the modifying element).

Conservation of mass, when applied to the species being diluted, gives $$F\iota C\iota = Fo Co \text{ or } F\iota = Fo(Co/C\iota) = Fo(1+2\Phi o/Fo)^{1/2} \qquad (3)$$

where Fι is the flow rate of the formulation at the exit defined by the catheter distal end, and Cι is the corresponding concentration at the exit. Detailed derivations of the equations above can be found in, for example, U.S. Pat. No. 4,298,003.

Modifying Agent Associated with Modifying Element

In one embodiment, modification is accomplished by incorporating a modifying agent as part of the catheter. In this embodiment, an agent is delivered through the catheter, contacts the modifying agent at some point in the flow path defined by the catheter, and is modified by the modifying agent of the modifying element prior to its release at the delivery site. The modifying element in this embodiment is that portion of the catheter comprising a modifying agent.

The modifying agent can be associated with at least an inner wall of the modifying element (i.e., a wall of the modifying element is in fluid communication with the catheter inner lumen defining the formulation flow path), and in some embodiments is incorporated into the body of the modifying element. As will be evident to the ordinarily skilled artisan, the modifying agent can be incorporated into the modifying element by impregnating, imbedding, coating, or chemically bonding the modifying agent on or within in the modifying element component as appropriate according to the component(s) with which the modifying agent is associated and the nature of the modifying agent. For example, the modifying agent can be coated on an inner wall, an outer wall, or both of the modifying element; impregnated in a modifying element wall; or any combination thereof. For example, the modifying agent can be a catalyst (e.g., an enzyme) immobilized on an inner surface of the modifying element, such that the immobilized catalyst serves to transform the agent into an active species prior to release of the agent from the catheter. Alternatively or in addition, the modifying agent may diffuse out of the catheter to reach with the diluent.

Where the modifying element is provided as a bulb- or ring-like element attached to the elongate body distal end, the modifying agent can also be provided as a solution, gel, semi-solid, or other material placed within a lumen or space defined by the modifying element (e.g., as a porous solid or semi-solid material within a lumen defined by the modifying element. The bulb- or ring-like element can be provided as an at least partially collapsible element to facilitate implantation.

Drug Delivery Devices

As discussed above, the catheter is generally associated with a drug delivery device. The drug delivery device supplies drug or therapeutic agent to the catheter for delivery to a delivery site.

The drug delivery device generally comprises a drug reservoir that holds drug or agents to be delivered. Thus, the device enables long-term drug delivery without the need to re-fill or re-position the device. As such, the drug delivery device may be external to the subject or may be implanted. Regardless of whether the device is external or implanted, the device is associated with the catheter. By associated is meant attached, connected or the like to provide a pathway between the drug delivery device and the catheter. The association may be accomplished by a variety of means, e.g., chemical, mechanical or other such means. An attachment element, e.g., between the drug delivery device and the catheter can provide the means of association.

The entire drug delivery system, e.g., the drug delivery device, the elongate body and the modifying element can be provided pre-assembled, separately or a combination thereof. In particular embodiments, the entire assembly or components thereof will be provided sterile. Sterility can be accomplished by a number of means commonly known to those of skill in the art, e.g., gamma sterilization, steam sterilization, ethylene oxide sterilization, plasma sterilization, and the like.

Drug delivery devices suitable for use in the invention may be based on any of a variety of modes of operation. For example, the drug release device can be based upon a diffusive system, a convective system, or an erodible system (e.g., an erosion-based system). For example, the drug release device can be an electromechanical pump, a gas-driven pump, an osmotic pump, an electroosmotic pump, a vapor pressure pump, or osmotic bursting matrix, e.g., where the drug is incorporated into a polymer and the polymer provides for release of drug formulation concomitant with degradation of a drug-impregnated polymeric material (e.g., a biodegradable, drug-impregnated polymeric material). In other embodiments, the drug release device is based upon an electrodiffusion system, an electrolytic pump, an electrochemical system, an effervescent pump, a piezoelectric pump, a hydrolytic system, etc.

Drug release devices based upon a mechanical or electromechanical infusion pump can also be suitable for use with the present invention. Examples of such devices include those described in, for example, U.S. Pat. Nos. 4,692,147; 4,360,019; 4,487,603; 4,360,019; 4,725,852, and the like. In general, the present methods of drug delivery can be accomplished using, for example, any of a variety of prefilled exchangeable or refillable, non-exchangeable pump systems. Pumps and other convective systems are generally preferred due to their generally more consistent, controlled release over time.

In one embodiment, the drug release device is a controlled drug release device in the form of an osmotically-driven device. Preferred osmotically-driven drug release systems are those that can provide for release of drug in a range of rates of from about 0.01 µl/day to about 100 µl/day (i.e., from about 0.0004 µl/hr to about 4 µl/hr), preferably from about 0.04 µl/day to about 10 µl/day, generally from about 0.2 µl/day to about 5 µl/day, typically from about 0.5 µl/day to about 10 µl/day. In one embodiment, the volume/time delivery rate is substantially constant and at a substantially consistent rate (e.g., delivery is generally at a rate±about 5% to 10% of the cited volume over the cited time period, e.g., a volume rate of about 500 µl/day is accomplished by delivery of about 200 µl/hour over a period of 24 hours, with the delivery rate over that 24 hours period fluctuating over that period by about ±5% to 10%). Exemplary osmotically-driven devices suitable for use in the invention include, but are not necessarily limited to, those described in U.S. Pat. Nos. 3,760,984; 3,845,770; 3,916,899; 3,923,426; 3,987,790; 3,995,631; 3,916,899; 4,016,880; 4,036,228; 4,111,202; 4,111,203; 4,203,440; 4,203,442; 4,210,139; 4,327,725; 4,627,850; 4,865,845; 5,057,318; 5,059,423; 5,112,614; 5,137,727; 5,234,692; 5,234,693; 5,728,396; and the like.

In one embodiment the controlled drug release device is an osmotic pump, e.g., an osmotic pump similar to that described in U.S. Pat. No. 5,728,396. In one embodiment of particular interest, the osmotic pump is a DUROS™ osmotic pump. In another embodiment of particular interest, the controlled drug release device is an electrolytic pump, such as provided by Microlin, and by Med-E-Cell™ as Infu-Disk™.

The catheter of the invention can also be used in conjunction with or as a component of a local concentration management system, as described in, for example, the U.S. patent application entitled "Local Concentration Management System," Attorney Docket No. DURE-023, filed on the same date as the instant specification.

Methods of Use

The catheter of the present invention is described herein primarily as used in drug delivery for simplicity and ease of disclosure. Any of a wide variety of drugs or therapeutic agents can be delivered using the present invention. Drugs suitable for use are generally in flowable formulations and are typically provided as liquids or semi-solids. The drugs may be anhydrous or aqueous solutions, suspensions or complexes and may be formulated with pharmaceutically acceptable vehicles or carriers, as well as inert or active ingredients. The drugs of formulations suitable for delivery using the present invention may be in various forms, such as uncharged molecules, components of molecular complexes or pharmacologically acceptable salts. Also, simple derivatives of the agents, e.g., prodrugs, esters, ethers, amides and the like, that are easily hydrolyzed by body pH, enzymes and the like can be employed. Preferably, the drugs are formulated so as to remain stable for long periods of time. As such, drugs or formulations of drugs may be stored in a drug reservoir in an inactive state and subsequently converted to an active state prior to delivery, e.g., during contact with the modifying element or modifying agent associated with the modifying element.

Other uses of the described invention will be apparent to others skilled in the art upon reading the present disclosure, however, and the present invention is intended to encompass such uses.

The diseases and conditions for which the present invention may find use vary. Of particular interest is the treatment of diseases or conditions that require long-term therapy, e.g., chronic or persistent diseases or conditions for which therapy involves treatment over a period of several days, weeks, months or years, up to the remaining lifetime of the subject. The present invention is particularly suited for long-term therapy, and in particular for therapy to treatment sites of the body inaccessible to conventional drug delivery devices or to fragile regions of treatment.

In the subject methods, the catheter is navigated to a delivery site within a subject, e.g. through biologically defined lumens, etc. Insertion of the catheter into the subject is generally accomplished in a manner similar to insertion of any of a variety of catheters known to those of ordinary skill in the art, e.g., under aseptic conditions, with at least some local or general anesthesia, under fluoroscopy, etc. The catheter preferably is associated with a drug delivery device which comprises a drug reservoir, and the assembly may be pre-loaded with drug or therapeutic agent. Pre-loading reduces start-up times, i.e., time related to movement of the drug or agent from the drug delivery device to the delivery site. This feature is particularly advantageous where the drug delivery device releases drug at a low or very low volume rate, e.g., in the range of about 0.1 µl per day to 200 µl per day. The pre-filled drug or agent may be the same or may be a different drug or agent as that which is to be delivered over the course of the treatment, or may be a different formulation thereof. The drug delivery device may be associated with the catheter at the beginning of the procedure. However, it is, of course, also possible to associate the drug delivery device with the catheter after the catheter has been positioned in the subject.

In practicing the subject methods, the catheter may be implanted in the subject for a chronic period (e.g., over several days, weeks, months or years). However, the catheter may also be designed for temporary use. The associated drug delivery device may be implanted in the subject or may be external to the subject and may be fixedly or removably attached to the catheter. Where the drug delivery device is removably attached, it may be removed following a desired treatment regime and where desirable, replaced with a similar or different drug or agent.

In certain embodiments, the drug delivery device and/or catheter may be anchored within the subject by any suitable means. For example, sutures can be used to secure the drug delivery device and/or catheter at or near an implantation site. Following implantation, the catheter defines a drug delivery conduit that provides for transport of drug or other therapeutic agent from the proximal end of the catheter to the distal end of the catheter, where the proximal end is preferably maintained at the initial access or implantation site and the catheter distal end is positioned at or near the treatment site.

Similarly, treatment sites and subjects may vary. For example, the catheter with associated drug delivery device may be used and/or implanted at any convenient site within a subject's body and oriented for delivery to any desired delivery site. For example, the catheter and/or drug delivery device may be partially or completely implanted in the subject, with at least a portion of the drug delivery device retained at an accessible, external or subcutaneous site within or outside the subject's body, e.g., under the skin of the arm, shoulder, groin, neck, back, leg or the like or within a surgically created or natural body cavity, e.g., within the mouth or surgically created pocket. Typically, the present invention will find use in subjects presently suffering from a disease or condition. However, subjects not presently suffering from a disease or condition, but who are susceptible to such, may also benefit from the present invention, for example for the delivery of prophylactic therapy regimes.

The catheter may be positioned at a site close (e.g., within a few inches or fraction(s) thereof, or at a site relatively distant, (e.g., more than about 5 inches, generally more than about 10 inches to 20 inches, typically more than about 40 inches) to a selected delivery site. A single catheter or a plurality of catheter assemblies can be used and/or implanted in a subject during the course of a treatment program depending on the extent of the treatment, the desirability of administering to multiple sites, and the like.

The device of the invention can be used to deliver any of a wide variety of substances. In one exemplary embodiment the device is used to deliver insulin (or a prodrug form of insulin that is modified during transit through the catheter of the invention), where the insulin (or a prodrug form) is contained in a drug delivery device, which is in turn operatively connected to a catheter of the invention. A distal end of the device catheter is implanted subcutaneously to provide for delivery of insulin to the subject.

Exemplary Embodiments

Exemplary embodiments of the invention are provided in the figures. Referring to FIG. 1, catheter 10 comprises an elongate body 20 having proximal end 21 defining inlet 22, distal end 23 defining outlet 24, and wall 25 defining a lumen or passageway 26, which passageway extends between the proximal and distal ends 21, 23. In this embodiment, elongate body 20 comprises a substantially impermeable portion 27 and a selectively water permeable modifying element 40. Selectively water permeable modifying element 40 allows water from the environment surrounding the catheter to diffuse into passageway 26, as indicated by arrows 74. As formulation introduced into inlet 22 flows through elongate body 20 in the direction of flow path 70 (indicated by arrow), the formulation is diluted as it passes through modifying element 40 (dilution of the formulation is represented schematically by change in arrow). The formulation can be diluted to a desired concentration at the outlet by varying, for example, the characteristics of the modifying element 40 (e.g., length, relative water permeability, dimensions relative to impermeable portion 27 (e.g., length, diameter, wall thickness, etc.), flow rate through the elongate body, and the like.

Figure 2:
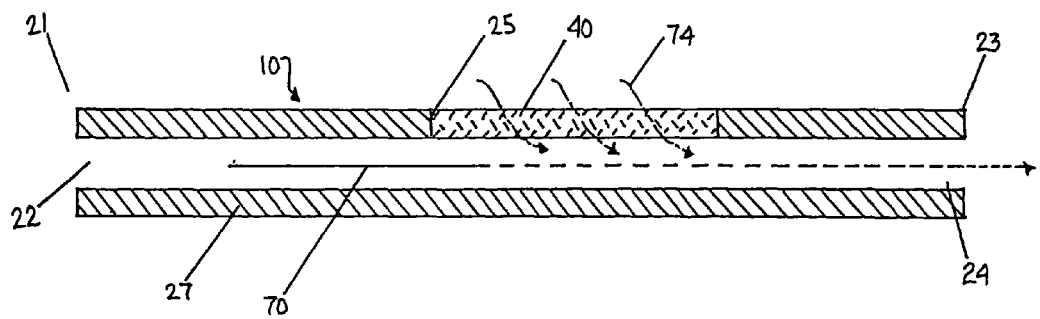
FIG. 2 is a cut-away view of a catheter of the invention comprising an elongate body comprising a selectively water permeable, patch-like modifying element positioned between the proximal and distal ends of the elongate body.

In FIG. 2, modifying element 40 is provided as a patch-like element positioned between proximal and distal ends 21, 23 of elongate body 20. While FIG. 2 indicates modifying element 40 is selectively water permeable, it will be readily understood that patch-like modifying elements can also comprise a modifying agent as described herein.

Figure 3:
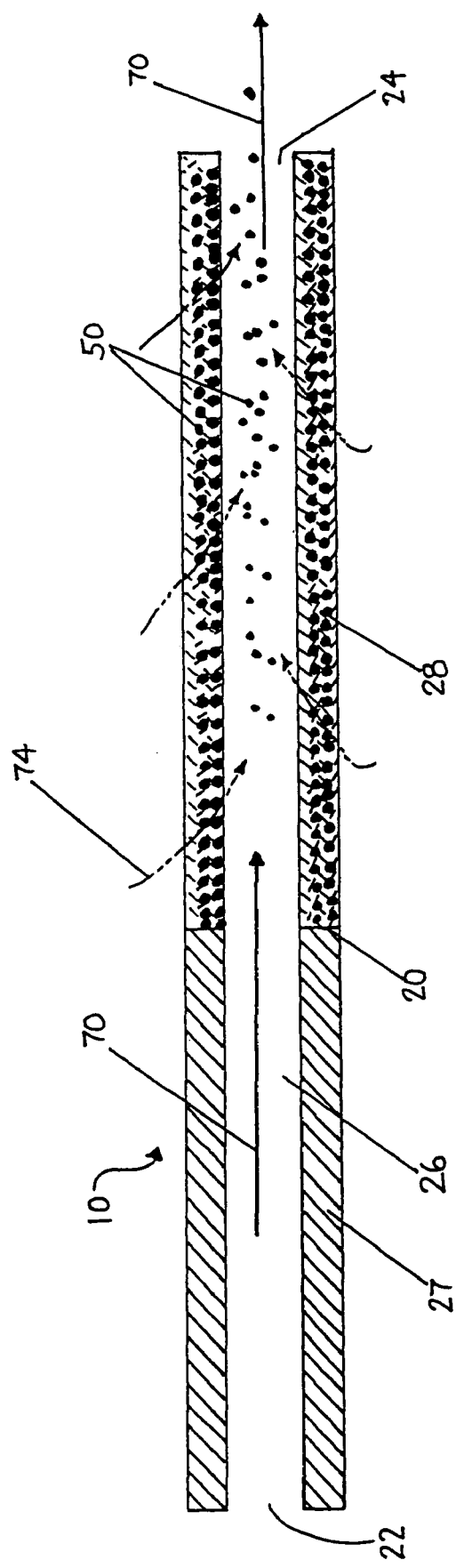
FIG. 3 is a cut-away view of an elongate body comprising a selectively water-permeable portion, which comprises a modifying agent which is solubilized and is combined with the agent in the flow pathway.
Figure 4:
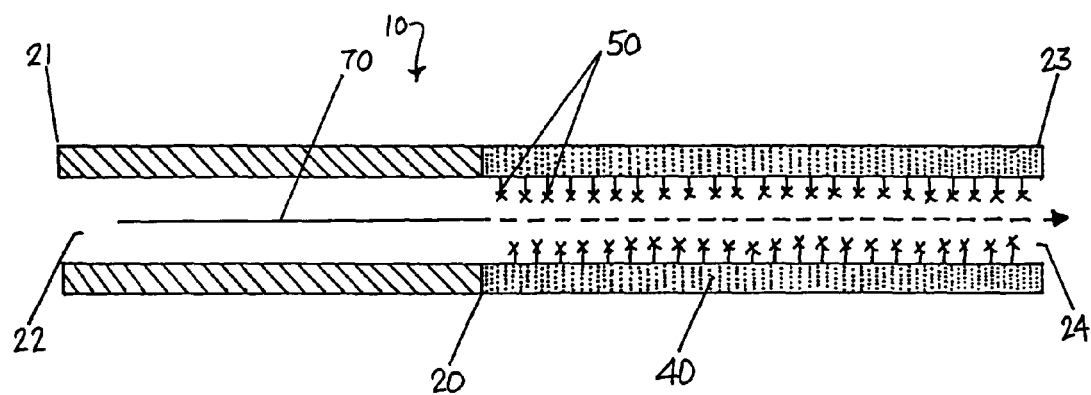
FIG. 4 is a cut-away view of an elongate body comprising a coating of modifying agent on the elongate body inner wall.

FIGS. 3 and 4 illustrate a catheter 10 of the invention comprising a modifying agent 50 incorporated into the modifying element 40 of catheter 10. In FIG. 3, elongate body 20 comprises a substantially impermeable portion 27 and a selectively water permeable modifying element 40, where the modifying element 40 comprises associated modifying agent 50. Diffusion of water through selectively water permeable modifying element 40 results in displacement of modifying agent 50 into passageway 26, resulting in mixing of formulation with modifying agent 50. As discussed above, modifying agent 50 can be, for example, a compound that alters the formulation pH, a pharmaceutically active agent for delivery with the agent(s) of the formulation, or a reagent/catalyst for reaction with a formulation component (e.g., an enzyme or other molecule to facilitate conversion of a prodrug in the formulation to an active drug).

In FIG. 4, modifying agent 50 is immobilized on an inner wall of at least a portion of modifying element 40, so that the modifying agent acts upon the formulation as is passes through modifying element 40 modifying element 40. In this embodiment, the modifying element may be substantially impermeable to formulation, formulation components, and to fluids in the environment of use, or may be selectively water permeable. Immobilization of modifying agent 50 can be accomplished by a variety of methods known in the art As illustrated in FIGS. 5 and 6, modifying element 40 can be provided as a ring-like or bulb-like element defining a modifying element lumen 43, which is operatively associated with elongate body 20 of catheter 10 by, for example, an attachment element 60. In this embodiment, formulation flows in the direction of arrow 70a through elongate body lumen 26, and out one or more outlets 24 positioned at a distal end of elongate body 20. Outlets 24 are in fluid communication with modifying element lumen 43. Modifying agent 50 is present within modifying element lumen 43, and may be coated on an inner wall of the modifying element, present as a solution or gel within lumen 43, or both. The material of modifying element 40 is substantially impermeable to modifying agent 50, but permeable to formulation or selectively permeable to modified formulation.

Formulation moves through and out of modifying element 40 as indicated by arrows 70b for delivery to the delivery site. FIG. 6 illustrates an embodiment in which modifying element 40 is provided as a bulb-like element, which element can be coated and/or filled with modifying agent 50. In the example in FIG. 6, modifying agent 50 is immobilized on an inner wall of modifying element 40. The embodiments of both FIGS. 5 and 6 also serve to increase the surface area over which the modified formulation is delivered, and thus may dilute or further dilute the formulation in the environmental fluids.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g., amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Example 1

Delivery of Baclofen HCl

A Baclofen HCl solution in DMSO (335.8 mg/cc) was delivered using a prototype of a catheter of the invention. With reference to the equations described herein, the dilution ratio was calculated, with Co=335.8 mg/cc Baclofen, with K $\Pi o$=31.3 μl mils/cm$^2$ hr for the Silastic tubing (Dow Corning Q 4750). The outer diameter of the tubing (OD) was 0.047 in (0.0597 cm), while the inner diameter was inner diameter (ID) was 0.025 in (0.0317 cm). The mean diameter (calculated by taking the log average value due to variations in wall thickness) was 0.0443 cm, with a tubing wall thickness of 11 mils (0.0235 in minus 0.0125 in). The pumping rate was 20 microliters/day (0.083 μl/hr). The length of the elongate body catheter was 5.22 cm.

Using these values and Equation (2) above, $\Phi o$ is calculated to be 4.13 μl/hr. Using this value in Equation (3), the estimated flow rate at the exit of the Silasitc tubing (elongate body) should be $Ft$=0.083 $(1+2\times4.13/0.083)^{1/2}$=0.83 μl/hr. Thus, according to this calculation, the flow rate at the delivery outlet of the Silastic tubing is about 10 times greater than the flow rate at the inlet connected to the pump. From Equation (1), the dilution ration can be calculated as $Ct/Co$=0.1.

An osmotic pump (DUROS™) was connected to an elongate body comprising a catheter coupled with a length of Silastic™ tubing having the same ID and OD as described above. The pump was filled with baclofen HCl in 100% DMSO (drug concentration (Co) 336.5 mg/cc), with the pumping rate determined to be about 3.48 μl/day (0.145 μl/hr). A mark was placed on the catheter at 5.22 cm from the connector to the pump. The pump and the section of catheter up to the mark were immersed in a water bath at 37° C. for ten days, after which the pumps were removed. The catheter were clamped at slightly above the 5.22 cm marks, and cut with a pair of scissors. The drug solution above the 5.22 cm mark was collected in separate flaks. Each catheter was further rinsed three times with 150 μl deionized water using a Hamilton syringe. The drug solution and the rinse were combined with diluted to volume for HPLC analysis to determine drug concentration. The experimental values are provided in the table below.

| Pump test | Distance drug solution traveled above the 5.22 cm mark (cm) | Total volume of drug solution above 5.22 cm mark (cc) | Drug concentration (Ct) in Silastic catheter above the 5.22 cm mark (mg/cc) | Dilution Ratio Ct/Co (Co = 336.5 mg/cc) |
|---|---|---|---|---|
| Pump 1 | 5.3 | 0.0168 | 54.8 | 0.163 |
| Pump 2 | 7.5 | 0.0238 | 72.3 | 0.215 |

The calculated drug dilution ratio from equation (1) and the values of $\Phi o$ and Fo, $C t/C o=1/(1+2\times4.13/0.145)^{1/2}=0.131$. The experimental values for the dilution ratio Ct/Co were 0.163 and 0.215 from duplicate tests, which values are in the same order of magnitude and in good agreement with the calculated value. The main source of discrepancies between the predicted and actual values may be generally due to inaccuracies involved in estimating the $\Phi o$ or $K\Pi o$ values for the baclofen HCl solution. The $K\Pi o$ values, and hence the $\Phi o$ value, may have been overestimated.

The invention as shown and described is considered to be the one of the most practical and preferred embodiments. It is recognized, however, that the departures may be made therefrom which are within the scope of the invention and that obvious modifications will occur to one skilled in the art upon reading this disclosure.

What is claimed is:

1. A method for delivery of an agent to a delivery site in a subject, the method comprising the steps of:
    (a) implanting at a delivery site in a subject at least a distal portion of a catheter comprising: an elongate body comprising a proximal end defining an inlet, and a distal end defining an outlet, the elongate body defining a passageway extending between the proximal and distal ends, and a modifying element operatively associated with the elongate body such that at least an inner wall of the modifying element is in fluid communication with the elongate body passageway; wherein flowable formulation introduced into the elongate body inlet moves through the elongate body passageway, contacts the modifying element inner wall, and exits the catheter; and
    (b) introducing a formulation comprising an agent into the inlet of the elongate body; wherein the introduced formulation containing said agent flows through the elongate body passageway whereby the agent contacts the modifying element and undergoes a physical or chemical change to provide a modified agent that is then released at the delivery site in the subject.

2. The method of claim 1, wherein the modifying element is a ring-like element defining a modifying element lumen, wherein the modifying element is operatively attached to the elongate body distal end so that the modifying element lumen is in fluid communication with the elongate body passageway.

3. The method of claim 2, wherein the modifying element comprises a modifying agent.

4. The method of claim 3, wherein the modifying agent is immobilized on the inner wall of the modifying element.

5. The method of claim 1, wherein the modifying element comprises a modifying agent.

6. The method of claim 5, wherein the modifying agent is imbedded within a wall of the modifying element.

7. The method of claim 5, wherein the modifying agent is coated on the inner wall of the modifying element.

8. The method of claim 5, wherein the modifying agent is immobilized on an inner wall of the modifying element.

9. The method of claim 1, wherein the modifying element is selectively water permeable.

10. The method of claim 9, wherein the modifying element comprises a modifying agent within a wall of the modifying element.

11. The method of claim 1, wherein the modifying element is a patch present in a sidewall of the elongate body.

12. The method of claim 11, wherein the modifying element is selectively water permeable.

13. The method of claim 1, wherein the modifying element is a bulb-like element defining a modifying element lumen, wherein the modifying element is operatively attached to the elongate body distal end so that the modifying element lumen is in fluid communication with the elongate body passageway.

14. The method of claim 13, wherein the modifying agent is immobilized on the inner wall of the modifying element.

15. The method of claim 1, wherein the formulation is introduced into the inlet at a low volume rate.

16. The method of claim 1, wherein the elongate body passageway is at least partially filled with an agent formulation prior to said implanting.

17. The method of claim 1, wherein the modifying element is a conduit, which conduit is in fluid communication with the elongate body passageway.

18. The method of claim 1, wherein the elongate body passageway is adapted for delivery of agent at a low volume rate.

* * * * *